United States Patent
Heining et al.

(10) Patent No.: US 11,976,253 B2
(45) Date of Patent: May 7, 2024

(54) METHOD OF ISOLATING LIPIDS FROM A LYSED LIPIDS CONTAINING BIOMASS BY EMULSION INVERSION

(71) Applicants: EVONIK OPERATIONS GMBH, Essen (DE); DSM IP ASSETS B.V., Te Heerlen (NL)

(72) Inventors: Annika Heining, Karlstein am Main (DE); Martin Heining, Karlstein am Main (DE)

(73) Assignees: Evonik Operations GmbH, Essen (DE); DSM IP Assets B.V., Te Heerlen (NL)

( * ) Notice: Subject to any disclaimer, the term of this patent is extended or adjusted under 35 U.S.C. 154(b) by 735 days.

(21) Appl. No.: 17/055,083

(22) PCT Filed: May 2, 2019

(86) PCT No.: PCT/EP2019/061244
§ 371 (c)(1),
(2) Date: Nov. 12, 2020

(87) PCT Pub. No.: WO2019/219396
PCT Pub. Date: Nov. 21, 2019

(65) Prior Publication Data
US 2021/0163842 A1    Jun. 3, 2021

(30) Foreign Application Priority Data

May 15, 2018  (EP) .................................... 18172340

(51) Int. Cl.
| | | |
|---|---|---|
| C11B 1/10 | (2006.01) | |
| A23K 10/12 | (2016.01) | |
| A23K 20/158 | (2016.01) | |
| C11B 3/16 | (2006.01) | |
| C12N 1/06 | (2006.01) | |

(52) U.S. Cl.
CPC ............... *C11B 1/10* (2013.01); *A23K 10/12* (2016.05); *A23K 20/158* (2016.05); *C11B 3/16* (2013.01); *C12N 1/06* (2013.01)

(58) Field of Classification Search
CPC .... C11B 1/10; C11B 3/16; C11B 1/02; A23K 10/12; A23K 20/158; A23K 10/20; A23K 50/10; C12N 1/06
See application file for complete search history.

(56) References Cited

U.S. PATENT DOCUMENTS

| | | |
|---|---|---|
| 5,583,019 A | 12/1996 | Barclay |
| 5,622,710 A | 4/1997 | Binder et al. |
| 6,166,230 A | 12/2000 | Bijl et al. |
| 6,166,231 A | 12/2000 | Hoeksema |
| 6,255,505 B1 | 7/2001 | Bijl et al. |
| 6,410,281 B1 | 6/2002 | Barclay |
| 6,410,282 B1 | 6/2002 | Kumar et al. |
| 6,441,208 B2 | 8/2002 | Bijl et al. |
| 6,727,373 B2 | 4/2004 | Bijl et al. |
| 6,750,048 B2 | 6/2004 | Ruecker et al. |
| 6,977,167 B2 | 12/2005 | Barclay |
| 7,005,280 B2 | 2/2006 | Barclay |
| 7,011,962 B2 | 3/2006 | Barclay |
| 7,041,485 B2 | 4/2006 | Bouarab et al. |
| 7,163,811 B2 | 1/2007 | Behrens et al. |
| 7,252,979 B2 | 8/2007 | Behrens et al. |
| 7,351,558 B2 | 4/2008 | Ruecker et al. |
| 7,419,596 B2 | 9/2008 | Dueppen et al. |
| 7,431,952 B2 | 10/2008 | Bijl et al. |
| 7,470,527 B2 | 12/2008 | Streekstra et al. |
| 7,566,570 B2 | 7/2009 | Abril |
| 7,579,174 B2 | 8/2009 | Bailey et al. |
| 7,662,598 B2 | 2/2010 | Ruecker et al. |
| 7,732,170 B2 | 6/2010 | Bailey et al. |
| 7,776,375 B2 | 8/2010 | Bertholet et al. |
| 7,781,193 B2 | 8/2010 | Ruecker et al. |
| 7,968,737 B2 | 6/2011 | Kawashima et al. |
| 8,217,151 B2 | 7/2012 | Schaap et al. |
| 8,415,506 B2 | 4/2013 | Waibel et al. |
| 9,023,625 B2 | 5/2015 | Pottathil et al. |
| 9,045,785 B2 | 6/2015 | Pfeifer, III |
| 9,896,642 B2 | 2/2018 | Wittenberg et al. |
| 10,342,772 B2 | 7/2019 | Barker et al. |
| 10,364,207 B2 | 7/2019 | Barker et al. |
| 10,472,316 B2 | 11/2019 | McClements et al. |
| 10,531,679 B2 | 1/2020 | Rudinger et al. |
| 10,619,175 B2 | 4/2020 | Rabe et al. |
| 10,842,174 B2 | 11/2020 | Durhuus et al. |
| 11,124,736 B2 | 9/2021 | Triplett et al. |

(Continued)

FOREIGN PATENT DOCUMENTS

| | | |
|---|---|---|
| AU | 2011226731 | 9/2011 |
| EP | 1 178 118 | 2/2000 |

(Continued)

OTHER PUBLICATIONS

Non Final Office Action for copending U.S. Appl. No. 16/317,249, dated Mar. 31, 2023.
Amendment & Response for copending U.S. Appl. No. 16/317,249, filed May 8, 2023.
U.S. Appl. No. 18/010,795, filed Dec. 15, 2022, Diehl.
Request for Continued Examination for copending U.S. Appl. No. 16/473,249, filed Nov. 30, 2021.
Amendment & Response to Accompany Request for Continued Examination for copending U.S. Appl. No. 16/473,249, filed Nov. 30, 2021.
Response to Non Final Office Action for copending U.S. Appl. No. 16/956,453, filed Dec. 2, 2021.
Non Final Office Action for copending U.S. Appl. No. 17/055,047, dated Dec. 16, 2021.

(Continued)

*Primary Examiner* — Deborah D Carr
(74) *Attorney, Agent, or Firm* — Law Office of: Michael A. Sanzo, LLC

(57) ABSTRACT

The current invention relates to a method of separating lipids from a lipids containing biomass by demulsification under mild conditions, to an oil and to a delipidated biomass as obtained by such a method.

16 Claims, No Drawings

(56) References Cited

U.S. PATENT DOCUMENTS

| | | |
|---|---|---|
| 11,261,400 B2 | 3/2022 | Bahl et al. |
| 11,324,234 B2 | 5/2022 | Silva et al. |
| 11,352,651 B2 | 6/2022 | Diehl et al. |
| 11,414,621 B2 | 8/2022 | Heining et al. |
| 11,542,220 B2 | 1/2023 | Heining et al. |
| 2003/0143659 A1 | 7/2003 | Bijl et al. |
| 2007/0003686 A1 | 1/2007 | Fichtali et al. |
| 2008/0032360 A1 | 2/2008 | Bailey et al. |
| 2008/0032365 A1 | 2/2008 | Bailey et al. |
| 2008/0166780 A1 | 7/2008 | Barclay |
| 2008/0199923 A1 | 8/2008 | Barclay |
| 2008/0233239 A1 | 9/2008 | Avramis et al. |
| 2008/0305531 A1 | 12/2008 | Lam et al. |
| 2009/0326267 A1 | 12/2009 | Bijl et al. |
| 2010/0227042 A1 | 9/2010 | Penet et al. |
| 2011/0091947 A1 | 4/2011 | Kim et al. |
| 2011/0098356 A1 | 4/2011 | Leininger et al. |
| 2011/0124034 A1 | 5/2011 | Kuehnle et al. |
| 2011/0201683 A1 | 8/2011 | Bezelgues et al. |
| 2011/0295028 A1 | 12/2011 | Cherinko et al. |
| 2012/0016145 A1 | 1/2012 | D'Addario et al. |
| 2012/0059180 A1 | 3/2012 | Dueppen et al. |
| 2013/0065282 A1 | 3/2013 | Tran et al. |
| 2013/0102802 A1 | 4/2013 | Sathish et al. |
| 2013/0172590 A1 | 7/2013 | Pfeifer, III |
| 2014/0096437 A1 | 4/2014 | Crowell et al. |
| 2015/0104557 A1 | 4/2015 | Rusing et al. |
| 2015/0176042 A1 | 6/2015 | Dennis et al. |
| 2016/0052846 A1 | 2/2016 | Gooding et al. |
| 2016/0183565 A1 | 6/2016 | Rudinger et al. |
| 2016/0249642 A1 | 9/2016 | Rabe et al. |
| 2016/0289592 A1 | 10/2016 | Massetti et al. |
| 2016/0319218 A1 | 11/2016 | Leininger et al. |
| 2017/0137742 A1 | 5/2017 | Heiska et al. |
| 2017/0290356 A1 | 10/2017 | Silva et al. |
| 2017/0295823 A1 | 10/2017 | Rabe et al. |
| 2017/0295824 A1 | 10/2017 | Priefert et al. |
| 2017/0298318 A1 | 10/2017 | Rabe et al. |
| 2017/0303561 A1 | 10/2017 | Durhuus et al. |
| 2017/0306365 A1 | 10/2017 | Rabe et al. |
| 2018/0071658 A1 | 3/2018 | Hale et al. |
| 2018/0192669 A1 | 7/2018 | Wilson |
| 2018/0200644 A1 | 7/2018 | Lewis |
| 2019/0249108 A1 | 8/2019 | Cherinko |
| 2019/0300818 A1 | 10/2019 | Bärz et al. |
| 2019/0323043 A1 | 10/2019 | Diehl et al. |
| 2019/0390135 A1 | 12/2019 | Leininger et al. |
| 2020/0015500 A1 | 1/2020 | De Vriendt |
| 2020/0231896 A1 | 7/2020 | Bahl et al. |
| 2020/0231898 A1 | 7/2020 | Bärz et al. |
| 2020/0339498 A1 | 10/2020 | Heining et al. |
| 2020/0362373 A1 | 11/2020 | Leininger et al. |
| 2020/0383353 A1 | 12/2020 | Wilson et al. |
| 2020/0404938 A1 | 12/2020 | Heining et al. |
| 2021/0017467 A1 | 1/2021 | Adugna et al. |
| 2021/0024966 A1 | 1/2021 | Heining et al. |
| 2021/0171991 A1 | 6/2021 | Burja et al. |
| 2021/0207056 A1 | 7/2021 | Heining et al. |
| 2021/0386095 A1 | 12/2021 | Erickson et al. |
| 2022/0017929 A1 | 1/2022 | Priefert et al. |
| 2022/0017930 A1 | 1/2022 | Priefert et al. |
| 2023/0242836 A1 | 8/2023 | Diehl et al. |

FOREIGN PATENT DOCUMENTS

| | | | |
|---|---|---|---|
| EP | 1 252 324 | 10/2020 | |
| JP | H08 275793 | 10/1996 | |
| SU | 1446142 | 12/1988 | |
| WO | WO 91/07498 | 4/1991 | |
| WO | WO 94/08467 | 4/1994 | |
| WO | WO 97/36996 | 10/1997 | |
| WO | WO 97/37032 | 10/1997 | |
| WO | WO 01/53512 | 7/2001 | |
| WO | WO 01/54510 | 8/2001 | |
| WO | WO 2011/153246 | 12/2011 | |
| WO | WO 2012/109642 | 8/2012 | |
| WO | WO 2014/122087 | 8/2014 | |
| WO | WO 2014/122092 | 8/2014 | |
| WO | WO 2015/095688 | 6/2015 | |
| WO | WO 2015/095693 | 6/2015 | |
| WO | WO 2015/095694 | 6/2015 | |
| WO | WO 2015/095696 | 6/2015 | |
| WO | WO 2018/011275 | 1/2018 | |
| WO | WO 2018/011283 | 1/2018 | |
| WO | WO 2018/011286 | 1/2018 | |
| WO | WO 2018/013670 | 1/2018 | |
| WO | WO-2018011286 A1 * | 1/2018 | ............... A23D 7/00 |
| WO | WO 2018/122057 | 7/2018 | |
| WO | WO 2019/032880 | 2/2019 | |
| WO | WO 2019/048327 | 3/2019 | |
| WO | WO 2019/063669 | 4/2019 | |
| WO | WO 2019/121752 | 6/2019 | |
| WO | WO 2019/122030 | 6/2019 | |
| WO | WO 2019/122031 | 6/2019 | |
| WO | WO 2019/191544 | 10/2019 | |
| WO | WO 2019/191545 | 10/2019 | |
| WO | WO 2019/219443 | 11/2019 | |
| WO | WO 2020/036814 | 2/2020 | |
| WO | WO 2020/094750 | 5/2020 | |
| WO | WO 2020/094751 | 5/2020 | |
| WO | WO 2020/109472 | 6/2020 | |
| WO | WO 2020/123965 | 6/2020 | |

OTHER PUBLICATIONS

Request for Continued Examination for copending U.S. Appl. No. 16/317,305, filed Jan. 9, 2022.
Amendment & Response to Accompany Request for Continued Examination for copending U.S. Appl. No. 16/317,305, filed Jan. 9, 2022.
Non Final Office Action for copending U.S. Appl. No. 16/956,453 dated Aug. 2, 2021.
CFSTR (Continuous Flow Stirred Tank Reactor, Chapter 8, Sec. 2, pp. 1-2, published online Dec. 2010) (Year 2010).
Amendment & Response to Non Final Office Action for copending U.S. Appl. No. 17/055,047, filed Jan. 20, 2022.
Non Final Office Action for copending U.S. Appl. No. 16/956,453, dated Feb. 8, 2022.
Non Final Office Action for copending U.S. Appl. No. 16/317,249, dated Mar. 24, 2022.
Notice of Allowance for copending U.S. Appl. No. 17/055,047, dated Mar. 28, 2022.
Amendment & Response to Non Final Office Action for copending U.S. Appl. No. 16/956,453, filed Jun. 22, 2022.
Amendment & Response to Non Final Office Action for copending U.S. Appl. No. 16/317,249, filed Jun. 22, 2022.
Non Final Office Action for copending U.S. Appl. No. 16/317,249, dated Dec. 7, 2020.
Response to Office Action for copending U.S. Appl. No. 16/317,305, filed Dec. 11, 2020.
Restriction Requirement for copending U.S. Appl. No. 16/956,453, dated May 20, 2021.
Request for Continued Examination for copending U.S. Appl. No. 16/473,805, filed Jun. 10, 2021.
Amendment & Response to Accompany Request for Continued Examination for copending U.S. Appl. No. 16/473,805, filed Jun. 10, 2021.
Non Final Office Action for copending U.S. Appl. No. 16/317,305, dated Jun. 4, 2021.
Response to Restriction Requirement for copending U.S. Appl. No. 16/956,453, filed Jul. 14, 2021.
U.S. Appl. No. 16/469,286, filed Jun. 13, 2019, US-2020/0015500 A1, Jan. 16, 2020, De Vriendt.
U.S. Appl. No. 16/636,940, filed Feb. 6, 2020, US-2020/0362373 A1, Nov. 19, 2020, Leininger.
U.S. Appl. No. 16/886,691, filed May 28, 2020, US-2020/0383353 A1, Dec. 10, 2020, Wilson.
U.S. Appl. No. 16/956,820, filed Jun. 22, 2020, US-2020/0404938 A1, Dec. 31, 2020, Heining.

(56) References Cited

OTHER PUBLICATIONS

U.S. Appl. No. 17/042,788, filed Sep. 28, 2020, US-2021/0024966 A1, Jan. 28, 2021, Heining.
U.S. Appl. No. 17/042,791, filed Sep. 28, 2020, US-2021/0017467 A1, Jan. 21, 2021, Adugna.
U.S. Appl. No. 17/284,463, filed Apr. 10, 2021, Erickson.
U.S. Appl. No. 17/291,608, filed May 6, 2021, Priefert.
U.S. Appl. No. 17/291,610, filed May 6, 2021, Priefert.
Non Final Office Action for copending U.S. Appl. No. 16/317,305, dated Aug. 16, 2022.
Notice of Allowance for copending U.S. Appl. No. 16/956,453, dated Sep. 1, 2022.
Final Office Action for copending U.S. Appl. No. 16/317,249, dated Oct. 5, 2022.
Amendment & Response to Non Final Office Action for copending U.S. Appl. No. 16/317,305, filed Dec. 15, 2022.
Final Rejection for copending U.S. Appl. No. 16/317,305, dated Jan. 6, 2023.
Request for Continued Examination for copending U.S. Appl. No. 16/317,249, filed Feb. 3, 2023.
Amendment & Response to Accompany RCE for copending U.S. Appl. No. 16/317,249, filed Feb. 3, 2023.
Saien, et al., "Effect of aqueous phase pH on liquid-liquid extraction with impinging-jets contacting technique," *Journal of Industrial and Engineering Chemistry* 16:1001-1005 (2010).
Final Office Action for copending U.S. Appl. No. 16/317,305, dated Jan. 11, 2021.
Final Office Action for copending U.S. Appl. No. 16/473,805, dated Feb. 10, 2021.
Restriction Requirement for copending U.S. Appl. No. 16/644,443, dated Dec. 21, 2021.
Response to Restriction Requirement for copending U.S. Appl. No. 16/644,443, filed Feb. 21, 2021.
Non Final Office Action for copending U.S. Appl. No. 16/644,443, dated Apr. 26, 2021.
Amendment & Response to Final Office Action for copending U.S. Appl. No. 16/317,305, filed May 7, 2021.
Amendment & Response to Non Final Office Action for copending U.S. Appl. No. 16/317,249, filed May 7, 2021.
International Search Report for corresponding international application PCT/EP2019/061244 filed May 2, 2019.
Written Opinion of the International Searching Authority for corresponding international application PCT/EP2019/061244 filed May 2, 2019.
International Preliminary Report on Patentability for corresponding international application PCT/EP2019/061244 filed May 2, 2019.
International Search Report for PCT/EP2017/083712 filed Dec. 20, 2017, for copending U.S. Appl. No. 16/473,805.
Written Opinion of the International Searching Authority for PCT/EP2017/083712 filed Dec. 20, 2017, for copending U.S. Appl. No. 16/473,805.
International Preliminary Report on Patentability for PCT/EP2017/083712 filed Dec. 20, 2017, for copending U.S. Appl. No. 16/473,805.
European Search Report and Search Opinion for European application EP 17 15 8286 filed Feb. 28, 2017, counterpart of copending U.S. Appl. No. 16/473,805.
International Search Report for PCT/EP2017/067570, filed Jul. 12, 2017; for copending U.S. Appl. No. 16/317,249.
Written Opinion of the International Searching Authority for PCT/EP2017/067570, filed Jul. 12, 2017; for copending U.S. Appl. No. 16/317,249.
International Preliminary Report on Patentability for PCT/EP2017/067570, filed Jul. 12, 2017; for copending U.S. Appl. No. 16/317,249.
International Search Report for PCT/EP2017/067585, filed Jul. 12, 2017; for copending U.S. Appl. No. 16/317,305.
Written Opinion of the International Searching Authority for PCT/EP2017/067585, filed Jul. 12, 2017; for copending U.S. Appl. No. 16/317,305.
International Preliminary Report on Patentability for PCT/EP2017/067585, filed Jul. 12, 2017; for copending U.S. Appl. No. 16/317,305.
International Search Report for PCT/EP2018/073323, filed Aug. 30, 2018, for copending U.S. Appl. No. 16/644,443.
Written Opinion of the International Searching Authority for PCT/EP2018/073323, filed Aug. 30, 2018, for copending U.S. Appl. No. 16/644,443.
International Preliminary Report on Patentability for PCT/EP2018/073323, filed Aug. 30, 2018, for copending U.S. Appl. No. 16/644,443.
European Search Report and Search Opinion for European application EP 17 19 6348 filed Oct. 13, 2017, counterpart of copending U.S. Appl. No. 16/644,443.
International Search Report for PCT/EP2018/085606 filed Dec. 18, 2018, for copending U.S. Appl. No. 16/956,453.
Written Opinion of the International Searching Authority for for PCT/EP2018/085606 filed Dec. 18, 2018, for copending U.S. Appl. No. 16/956,453.
International Preliminary Report on Patentability for for PCT/EP2018/085606 filed Dec. 18, 2018, for copending U.S. Appl. No. 16/956,453.
European Search Report and Search Opinion for European application EP 18 15 6840 filed Feb. 15, 2018, counterpart of copending U.S. Appl. No. 16/956,453.
International Search Report for, PCT/EP2019/061629 filed May 7, 2019, for copending U.S. Appl. No. 17/055,047.
Written Opinion of the International Searching Authority PCT/EP2019/061629 filed May 7, 2019, for copending U.S. Appl. No. 17/055,047.
International Preliminary Report on Patentability for PCT/EP2019/061629 filed May 7, 2019, for copending U.S. Appl. No. 17/055,047.
Hu, et al., "A review of recent developments of pre-treatment technologies and hydrothermal liquefaction of microalgae for bio-crude oil production," *Renewable and Sustainable Energy Reviews* 101:476-492 (2019).
Restriction Requirement for copending U.S. Appl. No. 16/317,305, dated May 19, 2020.
Office Action for copending U.S. Appl. No. 16/473,805, dated May 28, 2020.
Restriction Requirement for copending U.S. Appl. No. 16/317,249, dated Jun. 24, 2020.
Response to Restriction Requirement for copending U.S. Appl. No. 16/317,305, filed Jul. 20, 2020.
Response to Restriction Requirement for copending U.S. Appl. No. 16/317,249, filed Aug. 24, 2020.
Office Action for copending U.S. Appl. No. 16/317,305, dated Aug. 13, 2020.
Response to Office Action for copending U.S. Appl. No. 16/473,805, filed Aug. 28, 2020.
U.S. Appl. No. 15/027,429, filed Apr. 5, 2016, US-2016/0249642 A1, Sep. 1, 2016, Rabe.
U.S. Appl. No. 15/315,094, filed Nov. 30, 2016, US-2018/0192669 A1, Jul. 12, 2018, Wilson.
U.S. Appl. No. 15/516,022, filed Mar. 31, 2017, US-2017/0295823 A1, Oct. 19, 2017, Rabe.
U.S. Appl. No. 15/516,023, filed Mar. 31, 2017, US-2017/0290356 A1, Oct. 12, 2017, Silva.
U.S. Appl. No. 15/516,024, filed Mar. 31, 2017, US-2017/0295824 A1, Oct. 19, 2017, Priefert.
U.S. Appl. No. 15/516,038, filed Mar. 31, 2017, US-2017/0298318 A1, Oct. 19, 2017, Rabe.
U.S. Appl. No. 16/309,632, filed Dec. 13, 2018, US-2019/0249108 A1, Aug. 15, 2019, Cherinko.
U.S. Appl. No. 16/317,249, filed Jan. 11, 2019, US-2019/0300818 A1, Oct. 3, 2019, Bärz.
U.S. Appl. No. 16/317,305, filed Jan. 11, 2019, US-2020/0231898 A1, Jul. 23, 2020, Bärz.
U.S. Appl. No. 16/473,805, filed Jun. 26, 2019, US-2019/0323043 A1, Oct. 24, 2019, Diehl.
U.S. Appl. No. 16/639,529, filed Feb. 14, 2020, Burja.
U.S. Appl. No. 16/644,443, filed Mar. 4, 2020, US-2020/0231896 A1, Jul. 23, 2020, Bahl.
U.S. Appl. No. 16/956,453, filed Jun. 19, 2020, US-2020/0339498 A1, Oct. 29, 2020, Heining.
U.S. Appl. No. 17/055,047, filed Nov. 12, 2020, Heining.

(56) References Cited

OTHER PUBLICATIONS

Non Final Office Action for copending U.S. Appl. No. 16/317,249, dated Jun. 12, 2023.
Non Final Office Action for copending U.S. Appl. No. 16/317,249, dated Jun. 30, 2023.
Request for Continued Examination for copending U.S. Appl. No. 16/317,305, filed Jun. 4, 2023.
Amendment & Response to Accompany RCE for copending U.S. Appl. No. 16/317,305, filed Jun. 4, 2023.
Final Office Action for copending U.S. Appl. No. 16/317,305, dated Aug. 3, 2023.
Amendment & Response to Final Office Action for copending U.S. Appl. No. 16/317,305, filed Nov. 1, 2023.

* cited by examiner

METHOD OF ISOLATING LIPIDS FROM A LYSED LIPIDS CONTAINING BIOMASS BY EMULSION INVERSION

CROSS REFERENCE TO RELATED APPLICATIONS

The present application is US national stage of international application PCT/EP2019/061244, which had an international filing date of May 2, 2019, and which was published on Nov. 21, 2019. The PCT application claims priority to European application EP 18172340.4, filed on May 15, 2018. The contents of each of these applications is hereby incorporated by reference in its entirety.

The current invention relates to a method of separating lipids from a lipids containing biomass by demulsification under mild conditions.

PUFAs (polyunsaturated fatty acids) containing lipids are of high interest in the feed, food and pharmaceutical industry. Due to overfishing there is a high need for alternative sources for PUFAs containing lipids besides fish oil. It turned out that besides certain yeast and algal strains in particular microalgal cells like those of the order Thraustochytriales are a very good source for PUFAs containing lipids.

But with respect to microbial organisms and in particular cells of the order Thraustochytriales, which produce the PUFAs containing lipids, the isolation of the oil from the cells turned out as a particular problem. The most effective way of isolating the oil was the use of organic solvents like hexane. But the use of organic solvents leads to hazardous operating conditions, requires the use of expensive explosion-proof equipment and requires the implementation of an expensive solvent recovery process to avoid pollution of the environment.

In the attempt to avoid the use of organic solvents, as an effective alternative way for isolating the oil has turned out the salting-out of the oil with high amounts of sodium chloride. But the use of high amounts of sodium chloride leads to a delipidated biomass by-product which due to the high salt content cannot be utilized as a feed ingredient, so that the process is not very sustainable. Further, the high salt concentration leads to fast corrosion of the used steel equipment.

Thus, it was the object of the current invention to provide an effective method for isolating a lipid, in particular a PUFAs containing lipid, from lipids containing cells, in particular of the order Thraustochytriales, and simultaneously avoiding not only the need of organic solvents, but further avoiding the need of high amounts of salts and preferably also avoiding the use of high amounts of base and/or a high pH for realizing the effective isolation of the oil from the cells.

It was a further object of the current invention to provide a method for isolating a lipid, in particular a PUFAs containing lipid, from lipids containing cells, in particular of the order Thraustochytriales, and to provide simultaneously a delipidated biomass which can be utilized in a commercial way, preferably in the agricultural field.

It turned out that an effective separation of the lipid from the cell debris containing aqueous phase can surprisingly be realized, if the biomass, in particular after lysing, is concentrated, until the volume ratio between oil and water in the suspension exceeds the value of 1. By concentrating the suspension to such a high oil content, a spontaneous breaking of the emulsion as contained in the suspension does take place. This spontaneous breaking of the emulsion is also called "demulsification" or "emulsion inversion" in the context of this application.

The big advantage of this process is that it can be carried out without addition of solvents, without addition of salts like sodium chloride for salting out of the oil as well as without the addition of caustics, in particular without addition of caustics at high temperatures, so that an environmentally friendly, sustainable as well as mild method for isolating lipids from the cells is provided.

Thus, a first subject of the current invention is a method of isolating a lipid from a lipid containing biomass, comprising the following steps:
a) Providing a suspension of a biomass comprising cells which contain a lipid;
b) Optionally lysing the cells of the biomass;
c) Concentrating the suspension, until the volume ratio between oil and water in the suspension exceeds the value of 1;
d) Separating the oil containing light phase from the water, salts, cell debris and residual oil containing aqueous phase.

Preferably the suspension is concentrated, until the volume ratio between oil and water in the suspension reaches a value of between 1 and 2, more preferably of between 1 and 1.5, in particular of between 1 and 1.2.

In a preferred embodiment of the invention, the suspension is concentrated to a total dry matter (TDM) content of more than 60 wt.-%, preferably to a TDM content of between 60 and 98 wt.-% or of between 61 and 98 wt.-%, more preferably to a TDM content of between 60 and 80 wt.-% or of between 62 to 80 wt.-% or of between 62 and 85 wt.-% or of between 65 and 90 wt.-% or of between 65 and 80 wt.-%, in particular to a TDM content of between 60 and 75 wt.-% or of between 62 and 75 wt.-%.

According to the invention, concentration of the suspension is preferably carried out by evaporation of water at a temperature not higher than 100° C., preferably at a temperature of 70° C. to 100° C., more preferably 80° C. to 90° C.

Concentration of the suspension is preferably carried out in a forced circulation evaporator (for example available from GEA, Germany) to allow fast removal of the water.

According to the invention, after providing the suspension according to step (a) preferably a lysing step is carried out. The lysing step can be omitted, if—for example due to the fermentation conditions as applied—the cells or a big part thereof are/is already lysed or easily breakable in one of the following steps of the procedure without any explicit lysing step.

Lysing of the cells of the biomass can be carried out by methods as known to those skilled in the art, in particular enzymatically, mechanically, physically, or chemically, or by applying combinations thereof.

Depending on the time of exposure and/or the degree of force applied, a composition comprising only lysed cells or a composition comprising a mixture of cell debris and intact cells may be obtained. The term "lysed lipids containing biomass" insofar relates to a suspension which contains water, cell debris and oil as set free by the cells of the biomass, but beyond that may also comprise further components, in particular salts, intact cells, further contents of the lysed cells as well as components of a fermentation medium, in particular nutrients. In a preferred embodiment of the invention, only small amounts of intact cells, in particular less than 20%, preferably less than 10%, more preferably less than 5% (relating to the total number of intact cells as present before lysing the cells of the biomass) are present in the lysed biomass after the step of lysing the cells.

Lysing of the cells may be realized for example by utilizing a French cell press, sonicator, homogenizer, microfluidizer, ball mill, rod mill, pebble mill, bead mill, high pressure grinding roll, vertical shaft impactor, industrial blender, high shear mixer, paddle mixer, and/or polytron homogenizer.

In a preferred embodiment of the invention, lysing of the cells comprises an enzymatic treatment of the cells by applying a cell-wall degrading enzyme.

According to the invention, the cell-wall degrading enzyme is preferably selected from proteases, cellulases (e.g., Cellustar CL (Dyadic), Fibrezyme G2000 (Dyadic), Celluclast (Novozymes), Fungamyl (Novozymes), Viscozyme L (Novozymes)), hemicellulases, chitinases, pectinases (e.g., Pectinex (Novozymes)), sucrases, maltases, lactases, alpha-glucosidases, beta-glucosidases, amylases (e.g., Alphastar Plus (Dyadic); Termamyl (Novozymes)), lysozymes, neuraminidases, galactosidases, alpha-mannosidases, glucuronidases, hyaluronidases, pullulanases, glucocerebrosidases, galactosylceramidases, acetylgalactosaminidases, fucosidases, hexosaminidases, iduronidases, maltases-glucoamylases, xylanases (e.g., Xylanase Plus (Dyadic), Pentopan (Novozymes)), beta-glucanases (e.g., Vinoflow Max (Novozymes), Brewzyme LP (Dyadic)), mannanases, and combinations thereof. The protease may be selected from serine proteases, threonine proteases, cysteine proteases, aspartate proteases, metalloproteases, glutamic acid proteases, alcalases (subtilisins), and combinations thereof. The chitinase may be a chitotriosidase. The pectinase may be selected from pectolyases, pectozymes, polygalacturonases, and combinations thereof.

The adequate pH for utilizing the enzyme depends on the pH optimum of the enzyme.

In a preferred embodiment of the invention, an enzyme with a pH optimum of between 7.0 and 9.0, in particular of about 7.5, is used, so that the pH applied in this step is from 7.0 to 9.0, in particular from 7.0 to 8.0, preferably from 7.3 to 7.7. A preferred enzyme which can be used in this pH range is an alcalase.

The enzyme is preferably added as a concentrated enzyme solution, preferably in an amount of 0.01 to 1.5 wt.-%, more preferably in an amount of 0.03 to 1.0 wt.-%, above all in an amount of 0.05 to 0.5 wt.-%, relating to the amount of concentrated enzyme solution as added in relation to the total amount of the suspension after addition of the concentrated enzyme solution.

In a very preferred embodiment of the invention, lysing of the cells is carried out as follows:
i) Heating the suspension of (a) to a temperature of between 50° C. and 70° C., preferably to a temperature of between 55° C. and 65° C., and adding a cell wall-degrading enzyme to the fermentation broth, and adjusting an adequate pH value, if necessary, at which the enzyme is properly working;
ii) Keeping the temperature and pH in the ranges as depicted in (i) for at least one hour, preferably for at least two hours, more preferably for two to four hours.

In step (i), the enzyme can be added before or after heating up the suspension and/or before or after adjusting the pH. In the same way heating up of the suspension can be carried out before or after adjusting the pH.—But in a preferred embodiment, the enzyme is added after heating up of the suspension and after adjusting the pH, if adjusting of the pH is necessary, at all.—In a very preferred embodiment all measures are carried out more or less simultaneously.

Preferably, in the steps (i) and (ii) as well as in the method steps (b) and (c) of the invention, in general, the suspension is continuously mixed by using a stirrer and/or an agitator. In particular low shear agitation and/or axial-flow agitation may be applied, in particular as disclosed in WO 2015/095694. Impellers suitable for agitating include in particular straight blade impellers, Rushton blade impellers, axial flow impellers, radial flow impellers, concave blade disc impellers, high-efficiency impellers, propellers, paddles, turbines and combinations thereof.

The method according to the invention is preferably carried out at a pH of between 5 and 9, more preferably at a pH of between 5.5 and 8.5. Further, the temperature during the complete process is preferably not higher than 100° C., in particular below 90° C.

The method according to the invention preferably comprises as a further step the harvesting of the lipid, preferably of a PUFAs containing lipid, from the demulsified composition as obtained in step (c) by separation of the oil containing light phase from the water, salts, cell debris and residual oil containing heavy phase.

The harvesting of the lipid may comprise as an optional step the neutralization of the demulsified suspension, if the demulsification was not carried out at neutral pH before.

Neutralization of the demulsified composition is preferably realized, if needed or desired, by adding an acid, preferably sulfuric acid, or a caustic, in particular caustic soda, to adjust a pH value of 5 to 9, preferably 5.5 to 8.5, in particular 6.0 to 8.0 or 6.5 to 7.5. Before starting separation of the light phase from the heavy phase the neutralized composition may be stirred at neutral pH from several minutes up to several hours.

Separation of the oil containing light phase from the water, salts and cell debris containing heavy phase is preferably realized by mechanical means and preferably at a temperature of 60-90° C., more preferably 70-80° C., and at a pH value of preferably 6-9, more preferably 7-8.5. "Mechanical means" refers in particular to filtration and centrifugation methods as known to those skilled in the art.

After separation of the oil containing light phase, the oil thus obtained can further be worked up by applying methods as known to those skilled in the art, in particular refining, bleaching, deodorizing and/or winterizing.

In an alternative embodiment of the invention, instead of separating the oil containing light phase from the aqueous phase, the concentrated suspension itself might be used as a product, in particular as a feedstuff ingredient for feeding animals.

Thus a further subject of the current invention is a suspension containing cell debris, oil and water, wherein the amount of oil in the suspension is at least 50 wt.-%, in particular 50 to 75 wt.-%, wherein the oil is preferably an oil containing at least 20 wt.-%, preferably at least 30, 40 or 50 wt.-% of PUFAs and wherein the suspension is preferably characterized by containing less than 0.5 wt.-%, more preferably less than 0.2 or 0.1 wt.-% of solvents and/or by containing less than 1 wt.-%, more preferably less than 0.5 or 0.1 wt.-% of chlorides, in particular by being essentially free of solvents and chloride salts.

A particular advantage of the method of the current invention is that it can be carried out without the use of any organic solvent, in particular without the use of any polar or non-polar organic solvent. Thus, in a preferred embodiment of the invention, no or only little amounts of organic solvents, in particular of polar or non-polar organic solvents, are used for isolating the oil, in particular the PUFAs containing oil, from the biomass. Typical organic solvents are hexane and ethanol. In a preferred embodiment of the invention less than 2 wt.-% non-polar organic solvents are used, more preferably less than 1, 0.5 or 0.1 wt.-%. In a particularly preferred embodiment of the invention no non-polar organic solvent is used, at all. In a very preferred embodiment of the invention less than 2 wt.-% organic solvents are used, in general, particularly preferred less than 1, 0.5 or 0.1 wt.-%. In a particularly very preferred embodiment of the invention no organic solvents are used, at all, for isolating the PUFAs containing oil from the biomass.—This means in particular for this embodiment that the suspension as employed in the method according to the invention as well as all compositions as obtained by said single method steps preferably contain non-polar organic solvents, preferably organic solvents in general, in an amount of less than 2 wt.-%, more preferably less than 1 wt.-%, in particular less than 0.5 or 0.3 wt.-%, above all in an amount of less than 0.1 or 0.05 wt.-%.

A further advantage of the method of the current invention is that a very effective separation of the oil from the remaining biomass can be realized without the addition of sodium chloride, which is normally used for salting out the oil from the biomass. Preferably the method can be carried out without the addition of chloride salts, at all, above all without the addition of any salts for salting out the oil. But small amounts of chloride salts, in particular sodium chloride, might be present in the suspension due to the fermentation medium as used for growing of the biomass.

Thus, in a preferred embodiment of the current invention, no or only little amounts of sodium chloride are used for improving the oil isolation. In a preferred embodiment of the invention less than 1 wt.-% of sodium chloride, are used, more preferably less than 0.5 or 0.2 wt.-% of sodium chloride are used for isolating the oil from the biomass, above all less than 0.1 or 0.05 wt.-%, wherein the wt.-% relate to the total weight of the composition after addition of the sodium chloride. —This means in particular for this embodiment that the suspension as employed in the method according to the invention as well as all compositions as obtained by said single method steps preferably contain sodium chloride in an amount of less than 2 wt.-%, more preferably less than 1 wt.-%, in particular less than 0.5 or 0.3 wt.-%, above all in an amount of less than 0.1 or 0.05 wt.-%.

In a particularly preferred embodiment of the invention no or only little amounts of chloride salts are used for improving the oil isolation, at all. In this embodiment preferably less than 1 wt.-% of chloride salts, more preferably less than 0.5 or 0.2 wt.-% of chloride salts are used for isolating the oil from the biomass, above all less than 0.1 or 0.05 wt.-%, wherein the wt.-% relate to the total weight of the composition after addition of the chloride salts.

In a very preferred embodiment of the invention no or only little amounts of salts are used for improving the oil isolation, in general. In this embodiment preferably less than 1 wt.-% of salts, more preferably less than 0.5 or 0.2 wt.-% of salts are used for isolating the oil from the biomass, above all less than 0.1 or 0.05 wt.-%, wherein the wt.-% relate to the total weight of the composition after addition of the salts.—This means that preferably, in particular for this embodiment of the invention, that the suspension as employed in the method according to the invention as well as all compositions as obtained by said single method steps preferably contain salts in general in an amount of less than 2 wt.-%, more preferably less than 1 wt.-%, in particular less than 0.5 or 0.3 wt.-%, above all in an amount of less than 0.1 or 0.05 wt.-%.

A further advantage of the method of the current invention is that a very efficient separation of the oil from the remaining biomass can be realized without the addition of bases like caustic soda, which are normally used for breaking the emulsion. Preferably the method can be carried out without the addition of bases, at all, so that also no subsequent neutralization of the suspension is needed.—This does result in a biomass which contains only relatively small amounts of salts, in general, and by that comprises only a small amount of ashes. But small amounts of bases might be added, in particular for adjusting the pH, for example if the pH of the suspension is too low after the fermentation, or to facilitate the demulsification process.—That means that in a preferred embodiment of the invention no or only little amounts of bases are used in the methods according to the invention. In a preferred embodiment of the invention less than 4 wt.-% of bases, are used, more preferably less than 2 or 1 wt.-% of bases are used in the methods according to the invention, above all less than 0.5 or 0.2 wt.-%, wherein the wt.-% relate to the total weight of the composition after addition of the base.

But in an alternative embodiment of the invention caustics, in particular caustic soda, may be added, preferably in small amounts, to facilitate the demulsification and to increase the final oil yield.

As the demulsification can be carried out without the use of bases, in a preferred embodiment of the invention, the pH can preferably be kept during the complete procedure below a pH value of 9, in particular below 8.5, 8 or 7.5, which allows treatment of the lipid under very mild conditions and substantially reduces the degree of hydrolysis of the fatty acid esters as contained in the lipid.—Thus, in a preferred embodiment of the invention, the pH is kept during the complete procedure below 9, in particular in the range of 4.5 to 9, preferably below 8.5, 8 or 7.5, in particular in the range of 4.5 to 8.5, 4.5 to 8 or 4.5 to 7.5.

The methods of the current invention allow a very effective separation of the oil contained in the biomass from the cell-debris and other substances as contained in the fermentation broth. By using the methods of the current invention preferably more than 80 wt.-%, in particular more than 90 wt.-% of the oil contained in the biomass can be separated from the biomass and isolated.

It turned out that the oil as obtained by applying the method of the current invention has some advantageous characteristics over the PUFAs containing oils as disclosed in the state of the art so far. In particular it exhibits very low oxidation values, a very low content of free fatty acids and a very low content of polymerized triacylglycerols (TAGs). Free fatty acids and polymerized TAGs are undesirable by-products in the isolation of TAGs containing lipids, which preferably are avoided. Thus, a further subject of the current invention is an oil as obtained or as obtainable by a method according to the current invention.

A further subject of the current invention is therefore also an oil, in particular a PUFAs containing oil, which comprises fatty acid esters, in particular TAGs, in an amount of at least 50 wt.-%, preferably at least 70 or 80 wt.-%, in particular in an amount of at least 85 or 90 wt.-%, characterized by comprising free fatty acids (FFAs) in an amount of less than 0.6 wt.-%, preferably in an amount of less than 0.5 or 0.4 wt.-%, in particular in an amount of not more than 0.3 or 0.2 wt.-%.

A further subject of the current invention is therefore also an oil, which comprises TAGs in an amount of at least 50 wt.-%, preferably at least 70 or 80 wt.-%, in particular in an amount of at least 85 or 90 wt.-%, characterized by comprising polymerized TAGs in an amount of less than 1.0 wt.-%, preferably in an amount of less than 0.8 wt.-%, in particular in an amount of less than 0.6 wt.-%. A further subject of the current invention is therefore also a PUFAs containing oil, comprising TAGs in an amount of at least 50 wt.-%, preferably at least 70 or 80 wt.-%, more preferably at least 85 or 90 wt.-%, exhibiting the following characteristics: a) a content of free fatty acids (FFAs) of less than 0.6 wt.-%, preferably less than 0.5 or 0.4 wt.-%, in particular less than 0.3 or 0.2 wt.-%; b) a content of polymerized TAGs of less than 1.0 wt.-%, preferably less than 0.8 wt.-%, in particular less than 0.6 wt.-%; c) preferably a peroxide value of less than 0.5, in particular less than 0.3, very preferably less than 0.15; d) preferably an anisidine value of less than 15, in particular less than 10; e) preferably a content of moisture and impurities of less than 1 wt.-%, preferably less than 0.5 wt.-%; f) preferably a viscosity of less than 250 cps, more preferably of less than 200 cps, in particular of less than 160 cps; g) preferably a flash point of at least 350° C., more preferably of at least 400° C., in particular of at least 450° C.; h) preferably a content of omega-3 fatty acids, in particular of DHA and EPA, of at least 35 wt.-%, preferably at least 40 or 45 wt.-%, above all at least 50 wt.-%; i) preferably DHA and EPA each in an amount of at least 8 wt.-%, preferably at least 10 wt.-%, above all at least 15 wt.-%; j) preferably an amount of organic solvents of less than 0.5 wt.-%, more preferably less than 0.1 wt.-%, in particular less than 0.05 wt.-%, above all less than 0.01 wt.-%; k) preferably an amount of chlorides of less than 0.1 wt.-%, more preferably less than 0.05 wt.-%, in particular less than 0.01 wt.-%.

The anisidine value (AV) is determined in accordance with AOCS Official Method Cd 18-90. The AV is a measure for secondary reaction products of the fatty acids, such as aldehydes and ketones, that occur during oxidation of the oil.

The peroxide value (PV) is determined in accordance with the AOCS Official Method CD 8-53. The PV is a measure for primary reaction products, such as peroxide and hyperoxides, that occur during oxidation of the oil.—According to the invention the PV is measured in meq/kg.

The content of free fatty acids is determined in accordance with AOCS Official Method AOCS Ca 5a-40. The content of moisture is determined in accordance with AOCS Official Methods AOAC 930.15, 935.29. The content of insoluble impurities is determined in accordance with AOCS Official Method AOCS 3a-46. The amount of DHA and EPA is determined in accordance with AOCS Official Method AOCS Ce 1b-89. The amount of total fat is determined in accordance with AOCS Official Method AOCS 996.06. The amount of crude fat is determined in accordance with AOCS Official Methods AOAC 920.39, 954.02. The amount of polymerized TAGs (pTAGs) is determined by high performance size exclusion chromatography (HPSEC) in accordance with DGF method C-III 3c (10).

As the isolation of the oil is carried out by using no or only small amounts of caustics, the aqueous phase obtained as a by-product comprises preferably only a relatively small amount of salts and ashes.

As the isolation of the oil is further preferably carried out by using no or only small amounts of solvents and by also using no or only small amounts of sodium chloride, the aqueous phase obtained as a by-product is preferably substantially free of organic solvents and sodium chloride, as well. Thus, the aqueous phase can be utilized in different ways, either directly after separation of the oil phase or after further work-up like concentrating and/or drying.

A further subject of the current invention is therefore a lipids, in particular PUFAs, containing aqueous suspension, containing a biomass, preferably a delipidated biomass, as obtained or as obtainable by a method according to the current invention. A further subject of the current invention is therefore also a concentrate or a dried product as obtained or obtainable by concentrating and/or drying this aqueous suspension. When concentrating the aqueous suspension, it is preferably dried until a total dry matter (TDM) content of 20 to 60 wt.-% is reached.—In the following the expression "aqueous suspension according to the invention" refers to the aqueous phase as obtained after separation of the oil phase as well as to any concentrated suspensions of this aqueous phase as obtained by concentrating of this aqueous phase. Drying is preferably carried out by solvent evaporation, as described further below.

A further subject of the current invention is therefore also a lipids, in particular PUFAs, containing aqueous suspension, containing a biomass, in particular cell debris of a delipidated biomass, characterized by a content of salts and/or ashes of less than 15 wt.-%, preferably 4 to 12 wt.-%, in particular 6 to 10 wt.-%, and preferably characterized further by a content of non-polar organic solvents of less than 1 wt.-%, preferably less than 0.5 or 0.2 wt.-%, more preferably less than 0.1 or 0.05 wt.-%, above all less than 0.01 wt.-%, and preferably further characterized by a content of chloride ions of less than 1 wt.-%, preferably less than 0.5 or 0.2 wt.-%, more preferably less than 0.1 or 0.05 wt.-%.

A further subject of the current invention is therefore in particular also a lipids, in particular PUFAs, containing aqueous suspension, containing a biomass, in particular, cell debris of a delipidated biomass, characterized by a content of salts and/or ashes of less than 15 wt.-%, preferably 4 to 12 wt.-%, in particular 6 to 10 wt.-%, and preferably characterized further by a content of organic solvents of less than 1 wt.-%, preferably less than 0.5 or 0.2 wt.-%, more preferably less than 0.1 or 0.05 wt.-%, above all less than 0.01 wt.-%, and preferably further characterized by a content of chloride ions of less than 1 wt.-%, preferably less than 0.5 or 0.2 wt.-%, more preferably less than 0.1 or 0.05 wt.-%.

A preferred subject of the current invention is therefore also a lipids, in particular PUFAs, containing aqueous suspension, containing a Thraustochytrid biomass, in particular cell debris of a delipidated Thraustochytrid biomass, characterized by a content of salts and/or ashes of less than 15 wt.-%, preferably 4 to 12 wt.-%, in particular 6 to 10 wt.-%, and preferably characterized by a content of non-polar organic solvents of less than 1 wt.-%, preferably less than 0.5 or 0.2 wt.-%, more preferably less than 0.1 or 0.05 wt.-%, above all less than 0.01 wt.-%, and preferably further characterized by a content of chloride ions of less than 1 wt.-%, preferably less than 0.5 or 0.2 wt.-%, more preferably less than 0.1 or 0.05 wt.-%.

A particularly preferred subject of the current invention is therefore also a lipids, in particular PUFAs, containing aqueous suspension, containing a Thraustochytrid biomass, in particular, cell debris of a delipidated Thraustochytrid biomass, characterized by a content of salts and/or ashes of less than 15 wt.-%, preferably 4 to 12 wt.-%, in particular 6 to 10 wt.-%, and preferably characterized by a content of organic solvents of less than 1 wt.-%, preferably less than 0.5 or 0.2 wt.-%, more preferably less than 0.1 or 0.05 wt.-%, above all less than 0.01 wt.-%, and preferably further characterized by a content of chloride ions of less than 1 wt.-%, preferably less than 0.5 or 0.2 wt.-%, more preferably less than 0.1 or 0.05 wt.-%.

The aqueous suspensions of the invention as described before, which are obtained as a by-product in the methods according to the invention, preferably exhibit a total dry matter (TDM) content of 20 to 60 wt.-%, in particular of 25 to 55 wt.-%, more preferably of 30 to 50 wt.-%, as such concentrated suspensions turned out as particularly suitable for the applications of the invention as described below.

The aqueous suspensions of the invention can be used as a product for different purposes as disclosed further below.—Alternatively, the aqueous suspensions may also be worked up further to increase the overall oil yield. The further work-up and isolation of further oil may be carried out by using caustics, in particular by using caustic soda.

"Chloride" according to the invention refers to the amount of detectable chlorine. The amount of chlorine as present can be determined for example by elemental analysis according to DIN EN ISO 11885. The chlorine is present in the form of salts which are called "chlorides". The content of chloride as mentioned according to the invention—also called "chloride ions"—only refers to the amount of detectable chlorine, not to the amount of the complete chloride salt, which comprises besides the chloride ion also a cationic counterion.

The total dry matter content (TDM) is preferably determined by gravimetric analysis. For doing that, a sample of the homogeneous suspension with a specific volume is weighed before and after freeze-drying. The remaining weight of the dried sample corresponds to the total dry matter as contained in that specific volume of the suspension.

In a particularly preferred embodiment of the current invention the water, salts, residual oil and cell debris containing aqueous phase, which is obtained as by-product in the oil harvesting step as described before, is converted into a dried biomass by drying the biomass to a total dry matter content of more than 90 wt.-%.

Due to the method of manufacture, the biomass comprises a very low content of salts, preferably ashes, of less than 30 wt.-%, in particular less than 25 wt.-%, more preferably less than 20 wt.-%.

Thus, a further subject of the current invention is also a lipids, preferably PUFAs, containing biomass, in particular a delipidated biomass, characterized by a content of salts and/or ashes of less than 30 wt.-%, preferably 8 to 30 wt.-%, more preferably 12 to 25 wt.-%, in particular 15 to 20 wt.-%.

The biomass, in particular delipidated biomass, according to the invention is preferably characterized by a content of salts and/or ashes of less than 30 wt.-%, preferably 8 to 30 wt.-%, more preferably 12 to 20 wt.-%, in particular 15 to 20 wt.-%, and preferably a content of non-polar organic solvents of less than 2 wt.-%, preferably less than 1, 0.5 or 0.2 wt.-%, more preferably less than 0.1, 0.05 or 0.02 wt.-% and preferably further characterized by a content of chloride ions of less than 2 wt.-%, preferably less than 1, 0.5 or 0.2 wt.-%, more preferably less than 0.1 or 0.05 wt.-%.

Thus, a preferred subject of the current invention is also a lipids, in particular PUFAs, containing Thraustocyhtrid biomass, in particular a delipidated Thraustochytrid biomass, characterized by a content of salts and/or ashes of less than 30 wt.-%, preferably 8 to 30 wt.-%, more preferably 12 to 20 wt.-%, in particular 15 to 20 wt.-%, and preferably a content of non-polar organic solvents of less than 2 wt.-%, preferably less than 1, 0.5 or 0.2 wt.-%, more preferably less than 0.1, 0.05 or 0.02 wt.-% and preferably further characterized by a content of chloride ions of less than 2 wt.-%, preferably less than 1, 0.5 or 0.2 wt.-%, more preferably less than 0.1 or 0.05 wt.-%.

Thus, a particularly preferred subject of the current invention is also a lipids, in particular PUFAs, containing Thraustochytrid biomass, in particular a delipidated Thraustochytrid biomass, characterized by a content of ashes, in particular salts, of less than 30 wt.-%, preferably 8 to 30 wt.-%, more preferably 12 to 20 wt.-%, in particular 15 to 20 wt.-%, and preferably a content of organic solvents of less than 2 wt.-%, preferably less than 1, 0.5 or 0.2 wt.-%, more preferably less than 0.1, 0.05 or 0.02 wt.-% and preferably further characterized by a content of chloride ions of less than 2 wt.-%, preferably less than 1, 0.5 or 0.2 wt.-%, more preferably less than 0.1 or 0.05 wt.-%.

As preferably the preparation is carried out without the use of non-polar organic solvents, preferably without the use of any organic solvents, at all, and without the use of sodium chloride, preferably without the use of chloride salts, at all, the resulting biomass is preferably free of any non-polar organic solvents, preferably free of any organic solvents, in general, and further essentially free of any chloride ions, at all, wherein "essentially free" means that it contains chloride ions in an amount of less than 0.1 wt.-%, in particular in an amount of less than 0.05 wt.-%.

The biomass according to the invention exhibits preferably a moisture content of not more than 10 wt.-%, preferably not more than 5 wt.-%.

The biomass thus obtained preferably comprises lipids (crude fat) in an amount of about 3 to 14 wt.-%, in particular about 4 to about 14 wt.-%, preferably in an amount of about 4.5 to about 12 wt.-%, more preferably in an amount of about 5 to about 10 wt.-%. Further, the lipid preferably comprises at least one PUFA selected from DHA and EPA, more preferably a mixture of DHA and EPA, wherein the ratio of DHA to EPA is preferably between 3:2 to 4:1 and wherein the amount of DHA is preferably from 30 to 50 wt.-% of the total amount of lipids contained and the amount of EPA is preferably from 10 to 20 wt.-%. of the total amount of lipids contained. Accordingly, also the aqueous suspensions as described before are preferably characterized by being convertible by drying into a biomass with such a crude fat content and/or EPA content and/or DHA content by drying the aqueous suspension to a moisture content of not more than 10 wt.-%, preferably not more than 5 wt.-%.

The biomass preferably further comprises proteins and/or amino acids in an amount of 15 to 25 wt.-%, more preferably in an amount of 17 to 23 wt.-%, and exhibits preferably a crude protein content of 25 to 35 wt.-%. As the demulsification is carried out under mild conditions, the weight ratio of free amino acids to the sum of proteins and peptides is preferably less than 9:1, more preferably less than 5:1, in particular less than 1:1. Accordingly, also the aqueous suspensions as described before are preferably characterized by being convertible by drying into a biomass with such an amino acid and/or crude protein content and/or ratio of free amino acids to proteins and peptides by drying the aqueous suspension to a moisture content of not more than 10 wt.-%, preferably not more than 5 wt.-%.

The biomass preferably further exhibits a crude fiber content of less than 5 wt.-%, preferably less than 2 wt.-%, more preferably of about 0 wt.-%. Accordingly, also the aqueous suspensions as described before are preferably characterized by being convertible by drying into a biomass with such a crude fiber content by drying the aqueous suspension to a moisture content of not more than 10 wt.-%, preferably not more than 5 wt.-%.

The dried biomass is preferably a delipidated biomass, that means a biomass, of which the major part of the lipids have been removed, preferably by a process as disclosed in this application. As the separation of oil from the biomass is very effectively, the remaining oil in the biomass is preferably less than 20 wt.-%, preferably less than 15 wt.-%, more preferably less than 10 wt.-%, of the oil as originally contained in the biomass. But as the oil cannot be removed completely by such a process, a substantial amount of oil is still contained also in the delipidated biomass according to the invention. That means that the term "delipidated biomass" according to the invention refers to a lysed biomass, from which the major part of oil has been removed, preferably by a process or method as disclosed in this application, but which still contains a substantial part of lipids, in particular of PUFAs containing lipids, wherein the amount of lipids in the dried delipidated biomass is preferably from 3-14 wt.-%, in particular 4-14 wt.-%, preferably from 4.5-12 wt.-%, more preferably from 5-10 wt.-%. Thus, the "delipidated biomass" according to the invention might also be called a "partially delipidated biomass" or a "substantially delipidated biomass".

Thus, a further subject of the current invention is a method of obtaining a biomass which has a low content of salts, is substantially free of non-polar organic solvents, preferably free of organic solvents, in general, and which is further substantially free of sodium chloride, preferably free of chloride salts, in general, comprising the method steps as mentioned before.

Conversion of the water, salts, remaining oil and cell debris containing heavy phase, which is obtained as by-product in the oil harvesting step, into a dried biomass by drying the biomass to a total dry matter content of more than 90 wt.-%, can be carried out in different ways.

In a very preferred way, the transformation is carried out by concentration of the heavy phase to a dry matter content of 30-50 wt.-%, preferably 35-45 wt.-%, and subsequent spray granulation of the biomass by means of fluidized bed granulation. By doing that, in a very efficient way, a biomass with advantageous features can be obtained. Spray granulation by means of fluidized bed granulation is disclosed in more detail in EP13176661.0.

Concentration of the heavy phase to a dry matter content of 30-50 wt.-% is preferably carried out by solvent evaporation, in particular vacuum evaporation, and/or by using a rotary evaporator, a thin-film evaporator or a falling-film evaporator. A useful alternative to solvent evaporation is reverse osmosis.

As alternative to the spray-granulation other drying methods, in particular other convective drying methods, like tunnel drying or spray drying, in particular nozzle spray drying, or contact drying methods, like drum drying, or radiation drying methods, like infrared drying, of the concentrated heavy phase would be applicable alternatives, wherein by using those methods normally particles with a smaller or bigger diameter are obtained.

According to the invention, during the drying process, an anti-caking agent, in particular silica, preferably a hydrophobic or hydrophilic silica, may optionally be added to the biomass to prevent caking. For this purpose, the suspension, in particular fermentation broth, comprising biomass as well as the silica are preferably sprayed into the particular drying zone. Alternatively or additionally, the biomass may be mixed with the anti-caking agent after the drying process. With respect to the use of silica as anti-caking agent reference is made in particular to the patent application EP13187631.0.

Conversion of a fine-grained powder into a coarse-grained dust-free product can be realized by granulating processes. Conventional organic or inorganic auxiliaries or supports such as starch, gelatin, cellulose derivatives or similar substances, which are typically used in food processing or feed processing as binding agents, gelling agents or thickeners, may optionally be used in this subsequent granulation process. Further auxiliaries that are preferably used according to the invention are disclosed in WO 2016/050560, with carboxymethylcellulose being a particulary preferred binding agent.

After drying and optionally granulating and/or sieving of the biomass, the dried biomass is preferably stored or packed.

The particulate biomass of the invention as well as the aqueous suspensions of the invention can be used in different ways. For example, they can be used in order to produce a foodstuff or feedstuff. Alternatively they may be used directly as foodstuff or feedstuff.

A further subject matter of the present invention is therefore likewise a method for producing a feedstuff or foodstuff, in which a particulate biomass and/or an aqueous suspension according to the invention is used, and is preferably mixed with further feedstuff or foodstuff ingredients.

In a preferred embodiment of the invention, the particulate biomass and/or the aqueous suspension is used for producing a foodstuff or feedstuff, in which the biomass and/or the aqueous suspension is preferably mixed with other foodstuff or feedstuff ingredients and is then processed to give the foodstuff or feedstuff.

The mixture of biomass and/or aqueous suspension and other foodstuff or feedstuff ingredients is processed in a preferred embodiment by an extrusion process, in order to obtain portions of foodstuff or feedstuff ready for sale. Alternatively, a pelleting method may also be used.

A screw or twin-screw extruder is preferably employed in the extrusion process. The extrusion process is preferably carried out at a temperature of 80-220° C., particularly 100-190° C., a pressure of 10-40 Bar, and a shaft rotational speed of 100-1000 rpm, particularly 300-700 rpm. The residence time of the mixture introduced is preferably 5-30 seconds, in particular 10-20 seconds.

In a mode of the extrusion process which is preferred in accordance with the invention, the process comprises a compacting step and a compression step.

It is preferred to intimately mix the components with each other before carrying out the extrusion process. This is preferably carried out in a drum equipped with vanes. In this mixing step, a preferred embodiment includes an injection of steam, in particular so as to bring about the swelling of the starch which is preferably present.

Before being mixed with the biomass and/or aqueous suspension, the further foodstuff or feedstuff ingredients are preferably comminuted—if required—so as to ensure that a homogeneous mixture is obtained in the mixing step. The comminuting of the further foodstuff or feedstuff ingredients may be carried out, for example, using a hammer mill.

A further subject of the current invention is therefore a method of feeding animals, wherein a particulate biomass and/or an aqueous suspension according to the invention are provided to animals, preferably after mixing the particulate biomass and/or the aqueous suspension with further feedstuff ingredients, wherein the animals are preferably selected from poultry, swine, minks, ruminants, in particular from calves and beef cattle, sheep, goats, companion animals or animals hold in aquaculture.

Alternatively the biomass and/or aqueous suspension according to the invention may be used in land applications, in particular as (organic) fertilizer, NPC (nitrogen/phosphorous/potassium source), soil enhancer, plant enhancer and/or composting aid, for producing biogas, for wastewater treatment or as alternative fuel, in particular for cement kilns. It might be further used as part of a fermentation medium for producing microorganisms, in particular for producing further PUFAs containing biomass.

A further subject of the current invention is therefore a method for enhancing soil, wherein a particulate biomass and/or an aqueous suspension according to the invention are strewed on and possibly mixed with ground, in particular with farmland soil or garden soil.

A further subject of the current invention is therefore also a method for fertilizing and/or composting ground, in particular farmland or garden, wherein a particulate biomass and/or an aqueous suspension according to the invention are strewed on and possibly mixed with ground, in particular with farmland soil or garden soil.

A further subject of the current invention is therefore also a method for producing biogas, wherein a particulate biomass and/or an aqueous suspension according to the invention is subjected to microbial degradation under anaerobic conditions, in particular by making use of methanogenic bacteria.

A further subject of the current invention is therefore also a method for treatment of wastewater, wherein wastewater is mixed with a particulate biomass and/or an aqueous suspension according to the invention.

A further subject of the current invention is therefore also a method for producing microorganisms, in particular for producing a lipids containing biomass, wherein the lipids preferably comprise PUFAs, wherein a particulate biomass and/or aqueous suspension according to the invention is used as part of the fermentation medium.

The lipids containing cells according to the invention preferably contain in average at least 10 wt.-% of lipids, more preferably at least 20 or 30 wt.-% of lipids, in particular at least 40 or 50 wt.-% of lipids.

The lipids containing cells according to the invention preferably further contain polyunsaturated fatty acids (PUFAs).

The lipids, and in particular PUFAs, containing cells of the biomass are preferably microbial cells or plant cells. In a preferred embodiment of the invention, the cells are capable of producing the PUFAs due to a polyketide synthase system. The polyketide synthase system may be an endogenous one or, due to genetic engineering, an exogenous one.

Accordingly, "delipidated biomass" according to the invention refers to the residues of such a PUFAs containing cells comprising biomass, in particular as disclosed further below, after having been subjected to an oil isolation process, in particular as disclosed further before.

The plant cells may in particular be selected from cells of the families Brassicaceae, Elaeagnaceae and Fabaceae. The cells of the family Brassicaceae may be selected from the genus *Brassica*, in particular from oilseed rape, turnip rape and Indian mustard; the cells of the family Elaeagnaceae may be selected from the genus *Elaeagnus*, in particular from the species *Oleae europaea*; the cells of the family Fabaceae may be selected from the genus *Glycine*, in particular from the species *Glycine max*.

The microbial organisms which contain a PUFAs containing lipid are described extensively in the prior art. The cells used may, in this context, in particular be cells which already naturally produce PUFAs (polyunsaturated fatty acids); however, they may also be cells which, as the result of suitable genetic engineering methods or due to random mutagenesis, show an improved production of PUFAs or have been made capable of producing PUFAs, at all. The production of the PUFAs may be auxotrophic, mixotrophic or heterotrophic.

The biomass preferably comprises cells which produce PUFAs heterotrophically. The cells according to the invention are preferably selected from algae, fungi, particularly yeasts, bacteria, or protists. The cells are more preferably microbial algae or fungi.

Suitable cells of oil-producing yeasts are, in particular, strains of *Yarrowia, Candida, Rhodotorula, Rhodosporidium, Cryptococcus, Trichosporon* and *Lipomyces*.

Suitable cells of oil-producing microalgae and algae-like microorganisms are, in particular, microorganisms selected from the phylum Stramenopiles (also called Heterokonta). The microorganisms of the phylum Stramenopiles may in particular be selected from the following groups of microorganisms: Hamatores, Proteromonads, Opalines, Developayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinales, Pedinellales, Dictyochales), Chrysomeridales, Sarcinochrysidales, Hydrurales, Hibberdiales, and Chromulinales. Other preferred groups of microalgae include the members of the green algae and dinoflagellates, including members of the genus Crypthecodiurn.

The biomass according to the invention preferably comprises cells, and preferably consists essentially of such cells, of the taxon Labyrinthulomycetes (Labyrinthulea, net slime fungi, slime nets), in particular those from the family of Thraustochytriaceae. The family of the Thraustochytriaceae (Thraustochytrids) includes the genera *Althomia, Aplanochytrium, Aurantiochytrium, Botryochytrium, Elnia, Japonochytrium, Oblongichytrium, Parietichytrium, Schizochytrium, Sicyoidochytrium, Thraustochytrium*, and *Ulkenia*. The biomass particularly preferably comprises cells from the genera *Aurantiochytrium, Oblongichytrium, Schizochytrium*, or *Thraustochytrium*, above all from the genus *Schizochytrium*.

In accordance with the invention, the polyunsaturated fatty acid (PUFA) is preferably a highly-unsaturated fatty acid (HUFA).

The cells present in the biomass are preferably distinguished by the fact that they contain at least 20% by weight, preferably at least 30% by weight, in particular at least 35% by weight, of PUFAs, in each case based on cell dry matter.

According to the current invention, the term "lipid" includes phospholipids; free fatty acids; esters of fatty acids; triacylglycerides (TAGs); sterols and sterol esters; carotenoids; xanthophylls (e. g., oxycarotenoids); hydrocarbons; isoprenoid-derived compounds and other lipids known to one of ordinary skill in the art.—The terms "lipid" and "oil" are used interchangeably according to the invention.

In a preferred embodiment, the majority of the lipids in this case is present in the form of triglycerides, with preferably at least 50% by weight, in particular at least 75% by weight and, in an especially preferred embodiment, at least 90% by weight of the lipids present in the cell being present in the form of triglycerides.

According to the invention, polyunsaturated fatty acids (PUFAs) are understood to mean fatty acids having at least two, particularly at least three, C—C double bonds. According to the invention, highly-unsaturated fatty acids (HUFAs)

are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, with preferably at least 50% by weight, in particular at least 75% by weight and, in an especially preferred embodiment, at least 90% by weight of the PUFAs present in the cell being present in the form of triglycerides.

Preferred PUFAs are omega-3 fatty acids and omega-6 fatty acids, with omega-3 fatty acids being especially preferred. Preferred omega-3 fatty acids here are the eicosapentaenoic acid (EPA, 20:5ω-3), particularly the (5Z,8Z,11Z,14Z,17Z)-eicosa-5,8,11,14,17-pentaenoic acid, and the docosahexaenoic acid (DHA, 22:6ω-3), particularly the (4Z,7Z,10Z,13Z,16Z,19Z)-docosa-4,7,10,13,16,19-hexaenoic acid.

In a very preferred embodiment of the current invention, cells, in particular a *Schizochytrium* strain, is employed which produces a significant amount of EPA and DHA, simultaneously, wherein DHA is preferably produced in an amount of at least 20 wt.-%, preferably in an amount of at least 30 wt.-%, in particular in an amount of 30 to 50 wt.-%, and EPA is produced in an amount of at least 5 wt.-%, preferably in an amount of at least 10 wt.-%, in particular in an amount of 10 to 20 wt.-% (in relation to the total amount of lipid as contained in the cells, respectively). DHA and EPA producing *Schizochytrium* strains can be obtained by consecutive mutagenesis followed by suitable selection of mutant strains which demonstrate superior EPA and DHA production and a specific EPA:DHA ratio. Any chemical or nonchemical (e.g. ultraviolet (UV) radiation) agent capable of inducing genetic change to the yeast cell can be used as the mutagen. These agents can be used alone or in combination with one another, and the chemical agents can be used neat or with a solvent. Preferred species of microorganisms of the genus *Schizochytrium*, which produce EPA and DHA simultaneously in significant amounts, as mentioned before, are deposited under ATCC Accession No. PTA-10208, PTA-10209, PTA-10210, or PTA-10211, PTA-10212, PTA-10213, PTA-10214, PTA-10215.

The suspension of biomass according to the present invention is preferably a fermentation broth. The suspension, in particular the fermentation broth, has preferably a biomass density of at least 80 or 100 g/l, in particular of 80 or 100 g/l to 250 g/l, preferably at least 120 or 140 g/l, in particular 120 g/l or 140 g/l to 220 g/l, more preferably at least 160 or 180 g/l, in particular 160 g/l to 200 g/l (calculated as dry-matter content). Thus, the suspension may be obtained by culturing and growing suitable cells in a fermentation medium under conditions whereby the PUFAs are produced by the microorganism.

Methods for producing the biomass, in particular a biomass which comprises cells containing lipids, in particular PUFAs, particularly of the order Thraustochytriales, are described in detail in the prior art (see e.g. WO91/07498, WO94/08467, WO97/37032, WO97/36996, WO01/54510). As a rule, the production takes place by cells being cultured in a fermenter in the presence of a carbon source and of a nitrogen source, along with a number of additional substances like minerals that allow growth of the microorganisms and production of the PUFAs. In this context, biomass densities of more than 100 grams per litre and production rates of more than 0.5 gram of lipid per litre per hour may be attained. The process is preferably carried out in what is known as a fed-batch process, i.e. the carbon and nitrogen sources are fed in incrementally during the fermentation. When the desired biomass has been obtained, lipid production may be induced by various measures, for example by limiting the nitrogen source, the carbon source or the oxygen content or combinations of these.

In a preferred embodiment of the current invention, the cells are grown until they reach a biomass density of at least 80 or 100 g/l, in particular of 80 or 100 g/l to 250 g/l, preferably at least 120 or 140 g/l, in particular 120 g/l or 140 g/l to 220 g/l, more preferably at least 160 or 180 g/l, in particular 160 g/l to 200 g/l (calculated as dry-matter content). Such processes are for example disclosed in U.S. Pat. No. 7,732,170.

Preferably, the cells are fermented in a medium with low salinity, in particular so as to avoid corrosion. This can be achieved by using chlorine-free sodium salts as the sodium source instead of sodium chloride, such as, for example, sodium sulphate, sodium carbonate, sodium hydrogen carbonate or soda ash. Preferably, chloride is used in the fermentation in amounts of less than 3 g/l, in particular less than 500 mg/l, especially preferably less than 100 mg/l.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup.

Suitable nitrogen sources are both inorganic and organic nitrogen sources. Examples of inorganic nitrogen sources are nitrates and ammonium salts, in particular ammonium sulphate and ammonium hydroxide. Examples of organic nitrogen sources are amino acids, in particular glutamate, and urea.

In addition, inorganic or organic phosphorus compounds and/or known growth-stimulating substances such as, for example, yeast extract or corn steep liquor, may also be added so as to have a positive effect on the fermentation.

The cells are preferably fermented at a pH of 3 to 11, in particular 4 to 10, and preferably at a temperature of at least 20° C., in particular 20 to 40° C., especially preferably at least 30° C. A typical fermentation process takes up to approximately 100 hours.

After the fermentation has ended, the cells may be pasteurized in order to kill the cells and to deactivate enzymes which might promote lipid degradation. The pasteurization is preferably effected by heating the biomass to a temperature of 50 to 121° C., preferably 50 to 70° C., for a period of 5 to 80 minutes, in particular 20 to 60 minutes.

Likewise, after the fermentation is ended, antioxidants may be added in order to protect the PUFAs present in the biomass from oxidative degradation. Preferred antioxidants in this context are BHT, BHA, TBHA, ethoxyquin, beta-carotene, vitamin E, in particular tocopherol, and vitamin C. The antioxidant, if used, is preferably added in an amount of 0.001 to 0.1 wt.-%, preferably in an amount of 0.002 to 0.05 wt.-%, relating to the total amount of the fermentation broth after addition of the antioxidant.

WORKING EXAMPLES

Example 1

An unwashed cell broth containing microbial cells (*Schizochytrium* sp.) at a biomass density of over 100 g/l was heated to 60° C. in an agitated vessel. After heating up the suspension, the pH was adjusted to 7.5 by using caustic soda (50 wt.-% NaOH solution), before an alcalase (Alcalase® 2.4 FG (Novozymes)) was added in liquid form in an amount of 0.5 wt.-% (by weight broth). Stirring was continued for 3 hours at 60° C. After that, 1 kg samples of the lysed cell mixture were subsequently transferred into a rotation evaporator and heated to a temperature of 85° C. The different samples were concentrated in the rotation evaporator, until a total dry matter content of between 42 and 95 wt.-% was reached. After that stirring was continued for about one further hour at room temperature. Surprisingly the formation of two phases, an oil phase and an aqueous phase could be observed at a total dry matter content of more than 60 wt.-%. The oil phase could be directly separated from the aqueous phase by centrifugation. Centrifugation was carried out for 5 minutes at 12.000 g, if not indicated otherwise.

In the following tables the influence of different parameters on the yield of oil is disclosed.

TABLE 1

Influence of concentration on phase separation and oil yield

| Total Dry Matter [wt.-%] | Phase separation | Amount of isolated oil [wt.-%] | Free fatty acids [wt.-%] |
| --- | --- | --- | --- |
| 42.0 | no | — | — |
| 45.2 | no | — | — |
| 60 | no | — | — |
| 63 | yes | 85.3 | 0.4 |
| 72.6 | yes | 85.1 | 0.5 |
| 74.6 | yes | 85.3 | 0.4 |
| 79 | yes | 80.0 | 0.4 |
| 95 | yes | not det. | not det. |

As can be seen from table 1, an efficient phase separation, i.e. demulsification, takes place at a total dry matter content in the suspension of more than 60 wt.-%, leading to a yield of isolated oil of at least 80 wt.-%, wherein the oil contains only a relatively low amount of free fatty acids of not more than 0.5 wt.-%.

TABLE 2

Influence of mechanical measure on oil yield

| Total Dry Matter [wt.-%] | Centrifugal force [g] | Amount of isolated oil [wt.-%] | Free fatty acids [wt.-%] |
| --- | --- | --- | --- |
| 79.2 | 4000 | 80.0 | 0.4 |
| 73.8 | 4000 | 79.9 | not det. |
| 73.8 | 12000 | 88.0 | not det. |

As can be seen from table 2, the yield is improved, when a higher centrifugal force is applied. Centrifugation was carried out for 5 minutes, respectively.

TABLE 3

Influence of pH value on oil yield

| Total Dry Matter [wt.-%] | pH value | Amount of isolated oil [wt.-%] | Free fatty acids [wt.-%] | Ash [wt.-%] | Polymerized TAG [wt.-%] |
| --- | --- | --- | --- | --- | --- |
| 75.7 | 5 | 80.1 | 0.3 | 17 | not det. |
| 73.4 | 7 | 82.4 | 0.25 | 27 | not det. |
| 72.3 | 9 | 79.8 | 0.2 | 30 | 0.56 |

As can be seen from table 3, adjusting the pH value before carrying out the demulsification has no big influence on the oil yield, but using a lysed fermentation broth in the demulsification without addition of caustics results in a suspension with a relatively low content of ashes of less than 20 wt.-%. Further it can be learnt, that independent of the pH value very low contents of free fatty acids—as low as 0.2 wt.-%—can be realized by the methods according to the invention.—Furthermore it was found out that the methods according to the invention lead to products with a very low amount of polymerized TAGs.

The invention claimed is:

1. A method of isolating a lipid from a lipid containing biomass, comprising the following steps:
   a) providing an aqueous suspension of a biomass comprising cells which contain the lipid;
   b) optionally lysing the cells of the biomass;
   c) concentrating the suspension to a total dry matter (TDM) content of more than 60 wt. -%;
   d) separating the oil containing light phase from the aqueous phase.

2. The method of claim 1, wherein the suspension is concentrated to a total dry matter (TDM) content of between 65 and 80 wt.-%.

3. The method of claim 1, wherein concentration of the suspension is carried out by evaporation of water at a temperature not higher than 100° C.

4. The method of claim 1, wherein concentration of the suspension is carried out by evaporation of water at a temperature of between 70° C. and 100° C.

5. The method of claim 1, wherein cells of the biomass are lysed enzymatically, mechanically, chemically and/or physically.

6. The method of claim 1, wherein the suspension is provided as a fermentation broth with a biomass density of at least 80 g/l.

7. The method of claim 1, wherein the suspension is provided as a fermentation broth and/or with a biomass density of 160 g/l to 200 g/l.

8. The method of claim 1, wherein the cells of the biomass comprise an average of at least 10 wt.-% of lipids.

9. The method of claim 1, wherein the cells of the biomass comprise an average of at least 40 wt.-% of lipids.

10. The method of claim 1, wherein the cells which contain lipids comprise PUFAs containing lipid and are selected from algae, fungi, protists, bacteria, microalgae, plant cells, and mixtures thereof.

11. The method of claim 10, wherein the cells are from the family of Thraustochytrids.

12. The method of claim 1, wherein the method is carried out, without the addition of solvents or caustics.

13. The method of claim 1, wherein the method is carried out without the addition of any solvents, caustic soda or sodium hydroxide.

14. The method of claim 1, wherein the pH is kept below 9, during the complete process.

15. The method of claim 1, wherein the pH is kept between 4.5 and 8.5, during the complete process.

16. An oil, comprising triacylglycerols (TAGs) in an amount of at least 50 wt.-%, and free atty acids (FFAs) in an amount of less than 0.6 wt.-%, wherein the oil comprises polymerized TAGs in an amount of less than 1.0 wt.-%.

* * * * *